United States Patent [19]
Chung

[11] Patent Number: 6,042,736
[45] Date of Patent: Mar. 28, 2000

[54] METHOD FOR PREPARING SAMPLES FOR MICROSCOPIC EXAMINATION

[75] Inventor: Lee Chung, Hsin-Chu, Taiwan

[73] Assignee: Taiwan Semiconductor Manufacturing Co., Ltd., Hsin-Chu, Taiwan

[21] Appl. No.: 08/971,893

[22] Filed: Nov. 17, 1997

[51] Int. Cl.[7] ............................... B44C 1/22; H01L 21/00
[52] U.S. Cl. .................. 216/33; 216/39; 216/52; 216/60; 216/66; 216/85; 438/8; 438/691; 438/745
[58] Field of Search ..................... 216/33, 39, 52, 216/60, 66, 85; 438/8, 691, 692, 745, 712

[56] References Cited

U.S. PATENT DOCUMENTS

| | | | |
|---|---|---|---|
| 4,389,280 | 6/1983 | Mueller et al. | 438/719 X |
| 5,064,498 | 11/1991 | Miller | 438/753 X |
| 5,662,814 | 9/1997 | Sugino | 216/39 X |

*Primary Examiner*—William Powell
*Attorney, Agent, or Firm*—Tung & Associates

[57] ABSTRACT

The present invention provides a method for preparing samples for microscopic examination that requires a glass slide to be laminated to a sample substrate by an adhesive layer for polishing in a sample polishing process. A cavity can be first formed in the surface of the substrate by a focused ion beam technique to reveal a characteristic feature which needs to be examined. A wax-based material is then used to fill the cavity and to protect the characteristic feature before an adhesive layer is applied on top of the substrate for bonding a glass slide to the substrate. After the sample is sectioned in the polishing process to reveal a new cross-section that contains the characteristic feature, the protective coating of the wax-based material can be removed by a suitable solvent such that the characteristic feature is ready for microscopic examination. A suitable wax-based material can be a wax that is similar to a candle wax which can be easily removed by acetone.

20 Claims, 2 Drawing Sheets

METHOD FOR PREPARING SAMPLES FOR MICROSCOPIC EXAMINATION

FIELD OF THE INVENTION

The present invention generally relates to a method for preparing samples for microscopic examination and more particularly, relates to a method for preparing samples for the electron microscopic examination of a semiconductor structure wherein a focused ion beam (FIB) technique is used to first create a cavity in the structure for exposing a characteristic feature.

BACKGROUND OF THE INVENTION

In the study of electronic materials and processes for fabricating such materials into an electronic structure, a specimen of the electronic structure is frequently used for microscopic examination for purposes of failure analysis and device validation. For instance, a specimen of an electronic structure such as a silicon wafer is frequently analyzed in scanning electron microscope (SEM) and transmission electron microscope (TEM) to study a specific characteristic feature in the wafer. Such characteristic feature may include the circuit fabricated and the defect formed during the fabrication process. An electron microscope is one of the most useful equipment for analyzing the microscopic structure of semiconductor devices.

In preparing specimens of an electronic structure for electron microscopic examination, various polishing and milling processes can be used to section the structure until a specific characteristic feature is exposed. As device dimensions are continuously reduced to the sub-half-micron level, the techniques for preparing specimens for study in an electron microscope have become more important. The conventional methods for studying structures by an optical microscope cannot be used to study features in a modern electronic structure due to its unacceptable resolution.

In the FIB technique, focused ion beams can be used to either locally deposit or remove materials. When the cluster impacts the surface of an electronic structure, the cluster disintegrates into atoms which are then scattered over the surface to remove a surface layer of the material. Typical ion beams have a focused spot size of smaller than 100 nm when produced by a high intensity source. Sources of such high intensity ions can be either liquid metal ion sources or gas field ion sources. Both of these sources have a needle type form that relies on field ionization or evaporation to produce the ion beam. After the ion beam is produced, it is deflected in a high vacuum and directed to a desired surface area. The focused ion beams can be suitably used in the semiconductor processing industry in a cutting or attaching method to perform a circuit repair, a mask repair or a micromachining process. A cutting process is normally performed by locally sputtering a surface with a forced ion beam.

In an ion beam milling process, when a material is selectively etched by a beam of ions such as $Ga^+$ focused to a sub-micron diameter, the technique is often referred to as focused ion beam etching or milling. FIB milling is a very useful technique for restructuring a pattern on a mask or an integrated circuit, and for diagnostic cross-sectioning of microstructures. In a typical FIB etching process, a beam of ions such as $Ga^+$ is incident onto a surface to be etched and the beam can be deflected to produce a desirable pattern. The focused ion beam can be used to bombard a specimen surface such that a cavity can be formed on the surface of an electronic structure to review a characteristic feature of the structure for electron microscopic examination.

The FIB technique utilizes a primary beam of ions for removing a layer of material at a high current, and for observing the surface that was newly formed at a low current. The observation of the surface is made by detecting the secondary electrons emitted from the sample surface when the surface is bombarded by the ions. A detector is used to receive the secondary electrons emitted from the surface to form an image. The FIB method, even though can not produce an image of a high resolution like that obtainable in a SEM/TEM, can be used to sufficiently identify a newly formed cross-sectional surface which may contain the characteristic feature to be examined. The capability of the FIB technique for making observations down to a resolution of 5~10 nm enables the cutting of a precise plane in an electronic structure such that it may be later examined by a SEM or TEM technique at a higher resolution than that capable with FIB.

FIGS. 1A through 1E illustrate a conventional process of preparing a SEM/TEM sample of an electronic structure which is first cut precisely by FIB for electron microscope observation. Referring initially to FIG. 1A, wherein an electronic structure 10 is shown. The electronic structure 10 has a top surface 12 and a bottom surface 14 on a silicon substrate 16. On the top surface 10, a cavity 18 is formed by a focused ion beam which has sidewalls 20 and 22 formed at an angle of approximately 90° and 45°, respectively with the top surface 12. The FIB technique reveals a characteristic feature, i.e., a defect, located on the sidewall 20. A layer of adhesive 24 is then applied on the top surface 12 of the structure 10. This is shown in FIG. 1B.

It should be noted that when the adhesive layer 24 is applied, the adhesive not only on the top surface 12 but also covers fills up the cavity 18. In the next step of the process, a glass slide 28 is used to cover the top surface 12 of electronic structure 10 bonded by the adhesive layer 24. The function of the glass slide 28 is to protect the top surface 12 of the electronic structure 10 such that during a subsequent grinding process, the top surface 12 does not delaminate and thus destroying the cavity 18 and the characteristic feature situated on the sidewall 20. The glass/glue/electronic structure laminate is then mechanically polished by a polishing disc or a grinding wheel in a plane perpendicular to the planar surface of the electronic structure 10. The grinding process can be controlled by a periodic observation through the glass slide 28 in an optical microscope. During such observation, the sample can be tilted 90° to reveal a newly formed cross-section by the polishing process in order to determine the end point of the polishing process.

As shown in FIG. 1D, the polishing process is stopped when the electronic structure 10 is polished to reveal the sidewall 20 covered by a glue layer 24. In order to observe the characteristic feature on the sidewall 20, the glue layer 24 that covers the sidewall 20 must be removed. As shown in FIG. 1E, the removal process frequently damages the sidewall 20 by removing the characteristic feature together with the glue layer 24 and forming a new cross-section 28 without the characteristic feature.

The conventional process of preparing a SEM/TEM sample which is cut precisely by FIB first for microscopic observation by SEM/TEM, as shown in FIGS. 1A~1E, is therefore inadequate in providing a reliable sample surface. The glue layer 24 shown in FIGS. 1B~1E is necessary for bonding a glass slide 28 to the electronic structure 10. However, the glue layer inevitably fills up the cavity created by FIB and consequently, destroys the characteristic feature during a glue removal process.

It is therefore an object of the present invention to provide a method for preparing samples which is cut precisely by FIB first for microscopic examination during which a glass slide must be bonded to a sample surface that does not have the drawbacks or shortcomings of the conventional sample preparation methods.

It is another object of the present invention to provide a method for preparing samples which is cut precisely by FIB first for microscopic examination that requires the bonding of a glass slide to an electronic structure by an adhesive layer wherein a subsequent adhesive removal step does not affect the characteristic feature to be examined.

It is a further object of the present invention to provide a method for preparing samples which is cut precisely by FIB first for microscopic examination that requires a glass slide to be bonded to a substrate by an adhesive layer wherein the adhesive layer is prevented from entering into a cavity that was previously formed and contains a characteristic feature to be examined.

It is another further object of the present invention to provide a method for preparing samples which is cut precisely by FIB first for microscopic examination that requires a glass slide to be bonded to an electronic structure by an adhesive layer wherein a cavity prepared by FIB in a top surface of the structure is first filled by a material that can be subsequently removed by a solvent to prevent the intrusion of the adhesive into the cavity.

It is still another object of the present invention to provide a method for preparing samples which is cut precisely by FIB first for microscopic examination that requires a glass slide to be bonded to an electronic structure by an adhesive layer wherein a cavity formed in the top surface of the substrate is first filled by a wax-based material prior to the application of the adhesive layer.

It is yet another object of the present invention to provide a method for preparing samples which is cut precisely by FIB first for microscopic examination that requires a glass slide to be bonded to an electronic structure by an adhesive layer wherein a cavity formed in the top surface of the substrate is first filled by a wax-based material prior to the bonding of the glass substrate and the wax-based material is subsequently removed by a hydrocarbon solvent prior to the electron microscopic examination.

SUMMARY OF THE INVENTION

In accordance with the present invention, a method for preparing samples which is cut precisely by FIB first for microscopic examination that requires a glass slide to be bonded to a sample substrate by using an adhesive layer is provided wherein the characteristic feature revealed in a cavity formed in the top surface of the substrate is not destroyed by the adhesive layer.

In a preferred embodiment, a method for preparing samples which is cut precisely by FIB first for microscopic examination can be provided by the operating steps of first providing a substrate that has a characteristic feature in a top surface to be examined and creating a cavity by FIB to expose the characteristic feature, then filling the cavity with a second material dissolvable in a solvent to substantially cover the cavity, then laminating a glass plate to the substrate by an adhesive layer sandwiching the characteristic feature thereinbetween, then removing partially the substrate, the glass plate and the adhesive layer in a plane transverse to the planar surface of the substrate until the characteristic feature is substantially exposed, and then removing the second material by a solvent.

In another preferred embodiment, the present invention method for preparing samples which is cut precisely by FIB first for the microscopic examination of an electronic substrate can be carried out by the steps of first providing an electronic substrate that has a characteristic feature in a top surface to be examined, and creating a cavity in the top surface to expose the characteristic feature by a FIB, then filling the cavity with a wax-based material to substantially cover the cavity, then laminating a glass plate to the electronic substrate by an adhesive layer sandwiching the characteristic feature thereinbetween, then mechanically removing the electronic substrate, the glass plate and the adhesive layer in a plane transverse to the planar surface of the electronic substrate until the characteristic feature is substantially exposed, and removing the wax-based material by a solvent. A suitable solvent to be used for removing the wax-based material is a hydrocarbon solvent such as acetone.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention provides a method for preparing samples which is cut by FIB first for microscopic examination that requires a glass plate to be laminated to a substrate by an adhesive layer wherein a cavity is first formed on the top surface of the substrate by FIB to substantially reveal a characteristic feature to be examined that does not have the drawbacks and shortcomings of conventional sample preparation methods. In the present invention novel method, a wax-based material is first used to fill the cavity formed prior to the lamination process by the adhesive layer. This prevents the adhesive layer from later intruding into and filling the cavity and the potential damages which may be caused by the removal of the adhesive from the cavity to the characteristic feature. The wax-based material forms a protective coating for the cavity, i.e., or the characteristic feature in the cavity, such that the glue layer never touches the characteristic feature. The wax-based material can then be easily removed, after the sample is sectioned to reveal a cross-section that contains the characteristic feature, by a hydrocarbon solvent without causing damages to the characteristic feature.

Figure 1A:
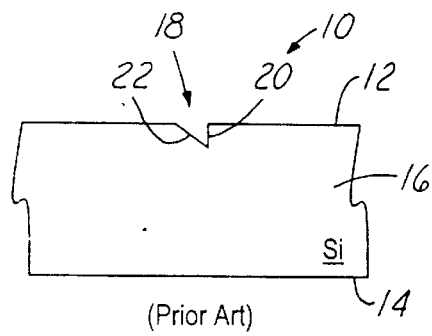
FIG. 1A is an enlarged, cross-sectional view of a conventional silicon substrate that has a cavity formed in a top surface by FIB.
Figure 1D:
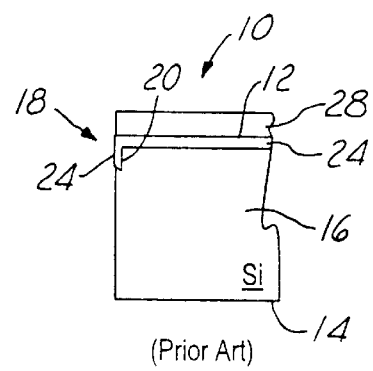
FIG. 1D is an enlarged, cross-sectional view of the conventional silicon substrate of FIG. 1C having partially the glass plate, the adhesive layer and the electronic structure removed in a plane transverse to the planar surface of the electronic substrate substantially exposing the characteristic feature to be examined.
Figure 1B:
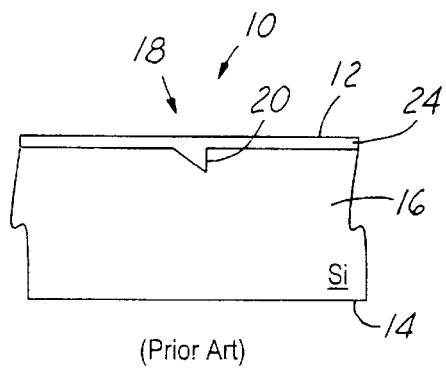
FIG. 1B is an enlarged, cross-sectional view of the conventional silicon substrate of FIG. 1A having its top surface coated with an adhesive layer.
Figure 1E:
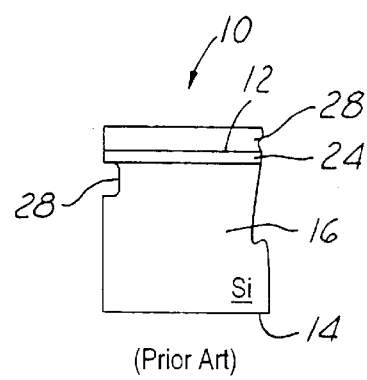
FIG. 1E is an enlarged, cross-sectional view of the conventional silicon substrate of FIG. 1D having both the glue layer that covered the characteristic feature and the characteristic feature itself removed in a glue layer removal process.
Figure 1C:
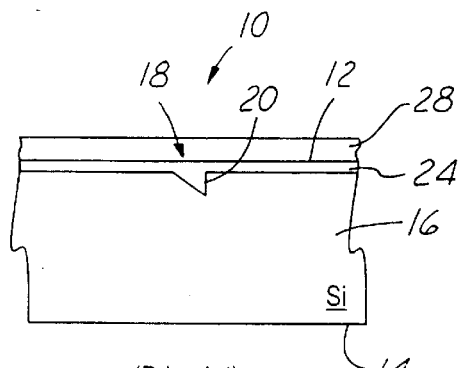
FIG. 1C is an enlarged, cross-sectional view of the conventional silicon substrate of FIG. 1B having a glass plate laminated on top of the electronic substrate by an adhesive layer.
Figure 2A:
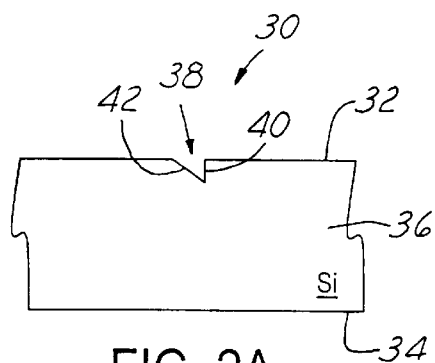
FIG. 2A is an enlarged, cross-sectional view of a present invention electronic substrate having a cavity formed in its top surface by FIB revealing a characteristic feature.

Referring now to FIG. 2A, wherein a present invention electronic structure 30 is shown. The electronic substrate 30 can be suitable formed of a silicon substrate 36. The silicon substrate 36 has a top surface 32 and a bottom surface 34. In the top surface 32, a cavity 38 is first formed with sidewalls 40, 42 by FIB. The sidewall 42 is formed at an angle of approximately 45° from the top surface 32. The FIB milling process can thus be stopped as soon as a characteristic feature is revealed in sidewall 40.

Figure 2B:
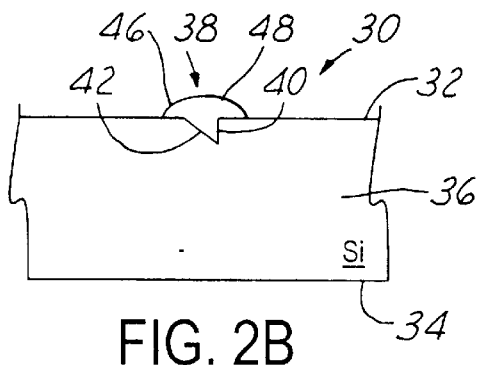
FIG. 2B is an enlarged, cross-sectional view of the present invention electronic substrate of FIG. 2A having the cavity filled with a material that can be later removed by a solvent.

After the successful formation of the cavity 38 by the FIB technique, as shown in FIG. 2B, a material 48 that can be removed by a solvent is deposited into the cavity 38 forming a heaping surface 46. A suitable material 48 that can be subsequently removed by a solvent is a wax-based material that can be easily removed by a hydrocarbon solvent. One of such hydrocarbon solvent may be acetone. The material 48 can be deposited into the cavity 38 in the following manner. The electronic structure 30 is first positioned on a hot plate (not shown) or on any other heating instrument that is capable of heating the structure to a temperature between about 80° C. and about 130° C. A preferred temperature is between about 100° C. and about 120° C. The temperature chosen is not very critical as long as it is high enough for the wax-based material to flow, and yet low enough to prevent the wax-based material from boiling. When the electronic structure 30 is heated to too high a temperature, the wax-based material can boil and thus causing air bubbles to be formed in the material 48 deposited. The wax-based material can be easily deposited into the cavity by touching the cavity lightly with the tip of a bar (not shown) of the wax-based material, and then withdrawing the bar from the surface of the electronic structure 30 as soon as a sufficient amount of the wax-based material has filled the cavity. The electronic structure 30 is then removed from the hot plate, or from any other heating instrument to allow the wax-based material to solidify and to securely bond to the cavity 38.

Figure 2F:
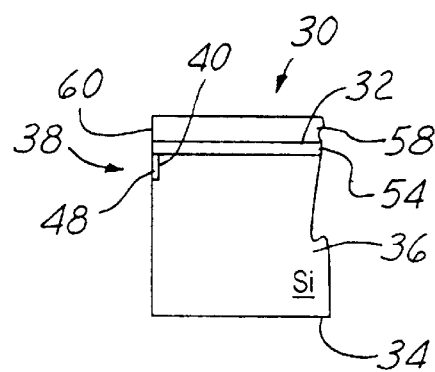
FIG. 2F is an enlarged, cross-sectional view of the present invention electronic substrate of FIG. 2E having partially the glass plate, the adhesive layer and the electronic substrate removed in a plane transverse to the planar surface of the substrate substantially revealing the characteristic feature covered by the material that is removable by a solvent.
Figure 2C:
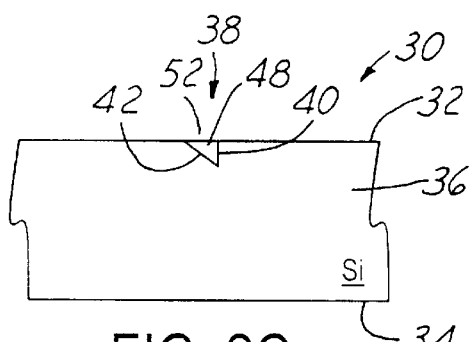
FIG. 2C is an enlarged, cross-sectional view of the present invention electronic substrate of FIG. 2B having the excess material that fills the cavity removed by a solvent.
Figure 2D:
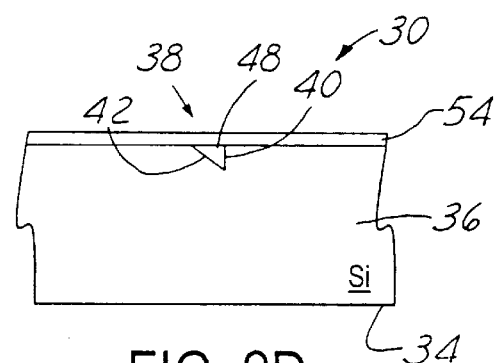
FIG. 2D is an enlarged, cross-sectional view of the present invention electronic substrate of FIG. 2C having an adhesive layer deposited on top.

In the next step of the process, as shown in FIG. 2C, the excess wax material 48 that protrudes above the top surface 32 of the silicon substrate 36 is removed. This removal of the wax-based material can be carried out by using a fiberless paper (not shown) that is wetted with a suitable solvent (such as acetone) to lightly scrap the top protruded surface 46 of the material 48. During such a scraping process, the excess wax-based material is dissolved by the acetone and is wiped off from the top surface 32 leaving a new surface 52 for the material 48 that is level with the top surface 32 of the silicon substrate 36. The wax-based material 48 securely covers the cavity 38 such that the characteristic feature situated on sidewall 40 is protected from the environment. During the next step of the process wherein an adhesive layer 54 is applied to the top surface 32 of the silicon substrate 36, as shown in FIG. 2D, the adhesive is prevented from entering the cavity 38. This novel feature of the present invention method substantially prevents the drawbacks of the conventional sample preparation method, i.e., the adhesive layer adheres to the characteristic feature in the cavity from happening.

In the next step of the present invention method, a glass slide 58 is bonded to the silicon substrate 36 by an adhesive layer 54. The adhesive used for forming layer 54 can be a polymeric-based adhesive and specifically, can be a thermoset-type polymeric adhesive. The glass slide 58 used is similar to those normally utilized in preparing biology samples for microscopic observation. It has a thickness of approximately 0.2 mm. The glass slide 58 prevents any damages that may occur to the top surface 32 of the substrate 36 during a subsequent grinding process for moving materials in a transverse direction of the electronic structure 30.

FIG. 2F shows an enlarged, cross-sectional view of the present invention electronic structure 30 having partially the glass plate 58, the adhesive layer 54 and the silicon substrate 36 removed in a plane transverse to the planar surface 32 of the substrate 36. The grinding or polishing process can be conducted by a mechanical grinding method utilizing a grinding wheel. The grinding process is stopped as soon as the wax-based material appears on the sidewall 40 when observed under an optical microscope which indicates an end point of the grinding process. The cavity 38 is therefore exposed which is still filled with the wax-based material 48 in a newly formed cross-sectional surface 60. It should be emphasized the fact that the characteristic feature to be examined is protected under the wax-based material layer 48 on the sidewall 40 of the cavity 38 is only made possible by the present invention novel method.

Figure 2G:
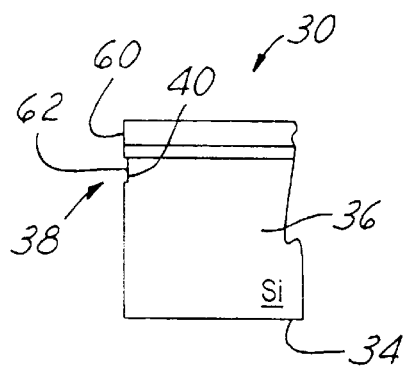
FIG. 2G is an enlarged, cross-sectional view of the present invention electronic substrate of FIG. 2F having the material that covered the characteristic feature removed by a solvent.
Figure 2E:
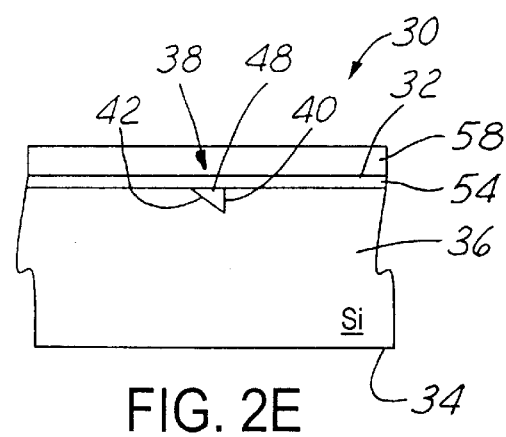
FIG. 2E is an enlarged, cross-sectional view of the present invention electronic substrate of FIG. 2D having a glass plate laminated on top of the electronic structure by the adhesive layer.
Figure 2H:
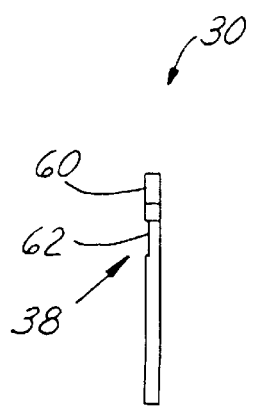
FIG. 2H is an enlarged, cross-sectional view of the present invention electronic substrate of FIG. 2G having the back side of the material removed for TEM examination.

In the final step of the present invention novel sample preparation method, as shown in FIG. 2G, the electronic structure 30 can be immersed in a suitable solvent for removal of the wax-based material 48 from sidewall 40. A suitable solvent can be a hydrocarbon solvent such as acetone. The newly exposed surface 62 of the sidewall 40 is now revealed with its characteristic feature which can be examined under an electron microscope. A suitable electron microscopic method to be used is either a scanning electron microscopy (SEM) method or a transmission electron microscopy (TEM) method. For further examination by TEM at a higher resolution, the structure 30 can be polished on the back side, as shown in FIG. 2H, to a thickness of between 600 Å for observation in a TEM.

The present invention novel sample preparation method has thus been amply demonstrated by the above descriptions and the appended drawings of FIGS. 2A–2G. It should be noted that, while a sample preparation method for electron microscopic examination is illustrated, the present invention novel method can be equally applied to any other microscopic test or any other optical test as long as a characteristic feature to be examined needs to be protected by a protective coating layer. The protective coating layer utilized does not have to be a wax-based material, any suitable material can be utilized as long as it can be easily applied and then removed subsequently by a solvent.

While the present invention has been described in an illustrative manner, it should be understood that the terminology used is intended to be in a nature of words of description rather than of limitation.

Furthermore, while the present invention has been described in terms of a preferred embodiment it is to be appreciated that those skilled in the art will readily apply these teachings to other possible variations of the inventions.

The embodiment of the invention in which an exclusive property or privilege is claimed are defined as follows:

1. A method for preparing samples for microscopic examination comprising the steps of:

providing a substrate having a characteristic feature in a top surface to be examined, removing a layer of a first material in said top surface and creating a cavity to expose said characteristic feature, filling said cavity with a second material which is dissolvable in a solvent, laminating a glass plate to said substrate by an adhesive layer sandwiching said characteristic feature thereinbetween, removing partially said substrate, said glass plate and said adhesive layer in a plane transverse to the planar surface of said substrate until said characteristic feature is substantially exposed, and removing said second material by a solvent to expose said characteristic feature.

2. A method according to claim 1, wherein said substrate is an electronic substrate.

3. A method according to claim 1, wherein said substrate is a silicon wafer and said characteristic feature is a defect formed in said wafer.

4. A method according to claim 1, wherein said layer of first material is removed by a micromachining method.

5. A method according to claim 4, wherein said micromachining method is a focused ion beam milling technique.

6. A method according to claim 1, wherein said second material is a wax-based material.

7. A method according to claim 1, wherein said second material is a wax having a melting temperature higher than 80° C.

8. A method according to claim 1, wherein said second material substantially covers said cavity by forming a hump over the top surface of said substrate.

9. A method according to claim 1, wherein said adhesive is a polymeric adhesive.

10. A method according to claim 1, wherein said step of removing said substrate, said glass plate and said adhesive layer in a transverse direction is performed by a grinding method with a grinding wheel.

11. A method according to claim 1, wherein said second material is removed by a hydrocarbon solvent.

12. A method according to claim 1, wherein said second material is removed by acetone.

13. A method for preparing samples for microscopic examination of an electronic substrate comprising the steps of providing an electronic substrate having a characteristic feature in a top surface to be examined, creating a cavity in said top surface to substantially expose said characteristic feature by a micromachining method, filling the cavity with a wax-based material to substantially cover the cavity, laminating a glass plate to said electronic substrate by an adhesive layer sandwiching said characteristic feature thereinbetween, mechanically removing said electronic substrate, said glass plate and said adhesive layer in a plane transverse to the planar surface of said electronic substrate until said characteristic feature is substantially exposed, and removing said wax-based material by a solvent.

14. A method according to claim 13, wherein said electronic substrate is a silicon wafer and said characteristic feature is a defect in a circuit formed in said wafer.

15. A method according to claim 13, wherein said micromachining method is a focused ion beam milling method.

16. A method according to claim 13, wherein said wax-based material is a petroleum-based wax having a melting temperature not less than 80° C.

17. A method according to claim 13, wherein said step of removing said substrate, said glass plate and said adhesive layer in a transverse direction is performed by a grinding method with a grinding wheel.

18. A method according to claim 13, wherein said wax-based material is removed by a hydrocarbon solvent.

19. A method according to claim 13, wherein said wax-based material is removed by acetone.

20. A method according to claim 13, wherein said adhesive layer is formed by a two-part thermoset adhesive.

* * * * *